US012778506B2

(12) United States Patent
Shimuta

(10) Patent No.: US 12,778,506 B2
(45) Date of Patent: Nov. 3, 2026

(54) BIOLOGICAL DATA MEASUREMENT SYSTEM

(71) Applicant: Murata Manufacturing Co., Ltd., Nagaokakyo (JP)

(72) Inventor: Toru Shimuta, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 312 days.

(21) Appl. No.: 18/470,762

(22) Filed: Sep. 20, 2023

(65) Prior Publication Data

US 2024/0008816 A1 Jan. 11, 2024

Related U.S. Application Data

(63) Continuation of application No. PCT/JP2022/016617, filed on Mar. 31, 2022.

(30) Foreign Application Priority Data

Apr. 30, 2021 (JP) ................................ 2021-077322

(51) Int. Cl.
*A61B 5/00* (2006.01)
*A61B 5/0205* (2006.01)
*A61B 5/1171* (2016.01)

(52) U.S. Cl.
CPC ............ *A61B 5/681* (2013.01); *A61B 5/0077* (2013.01); *A61B 5/0205* (2013.01);
(Continued)

(58) Field of Classification Search
CPC ...................................................... A61B 5/681
(Continued)

(56) References Cited

U.S. PATENT DOCUMENTS

| | | | | |
|---|---|---|---|---|
| 10,582,886 | B2 * | 3/2020 | Poeze ................ | A61B 5/02416 |
| 2016/0007865 | A1 | 1/2016 | Sakata et al. | |

(Continued)

FOREIGN PATENT DOCUMENTS

| | | | |
|---|---|---|---|
| JP | 2009247733 | A | 10/2009 |
| JP | 2010277611 | A | 12/2010 |

(Continued)

OTHER PUBLICATIONS

International Search Report in PCT/JP2022/016617, mailed May 10, 2022, 3 pages.

*Primary Examiner* — Nicole F Johnson
(74) *Attorney, Agent, or Firm* — ArentFox Schiff LLP

(57) ABSTRACT

A biological data measurement system is provided that includes an annular biosensor and a mobile control unit. The annular biosensor includes a body that has an annular shape and is configured to be worn on a finger and a sensor that measures, for example, a blood pressure. The mobile control unit includes an imager that captures images, and a display that prompts a user holding the mobile control unit in one hand to cause the imager to capture an image of a face of the user and another hand wearing the annular biosensor and displays the captured image. The mobile control unit also includes a controller that determines, based on the image, whether the other hand is at the height of a chest and controls the biological data measurement system based on the result of the determination to obtain data such as the blood pressure.

20 Claims, 10 Drawing Sheets

(52) U.S. Cl.
CPC .......... *A61B 5/1176* (2013.01); *A61B 5/7221* (2013.01); *A61B 5/7278* (2013.01); *A61B 5/7445* (2013.01); *A61B 2562/08* (2013.01)

(58) Field of Classification Search
USPC .......................................................... 600/301
See application file for complete search history.

(56) References Cited

U.S. PATENT DOCUMENTS

| | | | |
|---|---|---|---|
| 2016/0198955 A1 | 7/2016 | Fortin | |
| 2016/0281757 A1 | 9/2016 | Hofmann et al. | |
| 2018/0070863 A1 | 3/2018 | Matsumura et al. | |
| 2019/0076064 A1 | 3/2019 | Tahara et al. | |
| 2019/0307339 A1 | 10/2019 | Aelen | |
| 2019/0336017 A1 | 11/2019 | Robinson et al. | |
| 2020/0152312 A1* | 5/2020 | Connor | G06V 20/20 |
| 2020/0196881 A1* | 6/2020 | Zemel | A61B 5/02444 |
| 2020/0218312 A1* | 7/2020 | Connor | G06F 1/1649 |

FOREIGN PATENT DOCUMENTS

| | | | | |
|---|---|---|---|---|
| JP | 2017506158 | A | 3/2017 | |
| JP | 2017221350 | A | 12/2017 | |
| JP | 2018501016 | A | 1/2018 | |
| JP | 2020500052 | A | 1/2020 | |
| JP | 2020503087 | A | 1/2020 | |
| WO | 2014155750 | A1 | 10/2014 | |
| WO | 2016194330 | A1 | 12/2016 | |
| WO | WO-2018106839 | A2 * | 6/2018 | G16H 20/70 |

* cited by examiner

BIOLOGICAL DATA MEASUREMENT SYSTEM

CROSS REFERENCE TO RELATED APPLICATIONS

This application is a continuation of International Application No. PCT/JP2022/016617, filed Mar. 31, 2022, which claims priority to Japanese Patent Application No. 2021-077322, filed Apr. 30, 2021, the entire contents of each of which are hereby incorporated by reference in their entirety.

TECHNICAL FIELD

The present invention relates to a biological data measurement system.

BACKGROUND

When a site for blood pressure measurement is at a position higher than the heart, a measured blood pressure becomes lower by a difference in the hydrostatic pressure in the blood vessel due to gravity. On the other hand, when a site for blood pressure measurement is at a position lower than the heart, a measured blood pressure becomes higher by a difference in the hydrostatic pressure in the blood vessel. More specifically, when the site for blood pressure measurement changes up or down by 1 cm from the height of the heart, the blood pressure (e.g., the measured value) changes by about 0.7 mmHg.

As an example, Japanese Unexamined Patent Application Publication No. 2009-247733 (hereinafter "Patent Document 1") discloses an electronic sphygmomanometer including a camera that has a predetermined imaging range, performs an imaging operation while the blood pressure is measured, and outputs image data; a face-and-cuff detection unit that detects, based on the image data, whether a captured image indicated by the image data includes an image of a face and an image of a cuff; a positional information calculation unit that calculates positional information of the image of the face and the image of the cuff in the captured image; an improper use determination unit that performs a determination process of determining whether the electronic sphygmomanometer is properly used based on a positional relationship between the image of the face and the image of the cuff indicated by the calculated positional information; and an output unit that outputs the result of the determination process performed by the improper use determination unit. This electronic sphygmomanometer determines whether the electronic sphygmomanometer is properly used based on the positional relationship between the image of the face and the image of the cuff in the captured image during blood pressure measurement and, therefore, can detect whether the electronic sphygmomanometer is used in a proper manner, for example, in terms of the measurement accuracy.

Moreover, Japanese Unexamined Patent Application Publication No. 2020-500052 (hereinafter "Patent Document 2") proposes a device including a blood pressure sensor that obtains a measured blood pressure from a user holding the device in a hand; and a control unit that determines the angle of the device relative to the direction of gravity, identifies one or more positions of the user holding the device in the hand in a display image of the user with respect to a displayed predetermined positional range, determines the height of the blood pressure sensor relative to the height of the heart of the user based on the angle of the device relative to the direction of gravity and the one or more positions of the user in the image with respect to the predetermined positional range, and controls the device based on the height of the blood pressure sensor relative to the height of the heart of the user. This configuration makes it possible to measure a blood pressure by controlling the device based on the height of the blood pressure sensor relative to the height of the heart of the user.

However, the electronic sphygmomanometer disclosed in Patent Document 1 squeezes the upper arm with a cuff when measuring a blood pressure and is therefore invasive. Also, because the cuff is used, the size of the device (the electronic sphygmomanometer) is large, and the device is not suitable for portable use. For this reason, for example, the device cannot be used to measure a blood pressure while on the go.

On the other hand, with the device disclosed in Patent Document 2, the blood pressure is measured by holding the device in a hand and bringing a finger of the hand into contact with a blood pressure sensor. With this configuration, it is difficult to keep the contact pressure constant. If the contact pressure varies, the blood pressure at a measurement site contacting the blood pressure sensor fluctuates (although the contact pressure varies between measurement processes, the contact pressure particularly tends to vary during each measurement process), and it may become difficult to stably measure the blood pressure.

SUMMARY OF THE INVENTION

Accordingly, it is an object of the present invention to provide a biological data measurement system that is highly portable and can more accurately and non-invasively measure biological data including a blood pressure, the measurement of which is influenced by a difference between the height of a measurement site and the height of the heart (i.e., influenced by a hydrostatic pressure).

According to an exemplary aspect, a biological data measurement system is provided that includes an annular biosensor and a mobile control unit that are configured to communicate with each other. The annular biosensor includes a body that has an annular shape and is configured to be worn (i.e., "wearable") on a hand finger or a wrist and a sensor that is disposed in the body and measures at least a blood pressure. The mobile control unit includes an imager that captures images, a display that prompts a user holding the mobile control unit in a first hand to cause the imager to capture an image of a face of the user and a second hand wearing the annular biosensor and displays the image captured by the imager, and a controller that is configured to determine, based on the image, whether the second hand wearing the annular biosensor is at the height of a chest and to control the biological data measurement system based on the result of the determination.

With the biological data measurement system according to the exemplary aspects of the present invention, the annular biosensor having the annular shape and including the sensor is worn on a hand finger or a wrist. This configuration stabilizes a contact pressure (e.g., a pressing force) on a measurement site and thereby biological data including a blood pressure can be accurately measured. Also, because whether the second hand wearing the annular biosensor is at the height of the chest (heart) is determined based on the image obtained by capturing the face of the user and the second hand wearing the annular biosensor and because the biological data measurement system is controlled (biological data including the blood pressure is measured) based on the result of the determination, the biological data including the blood pressure can be more accurately measured. Furthermore, because no cuff is used, the biological data measurement system is highly portable and can non-invasively measure biological data including a blood pressure.

In general, the exemplary aspects of the present invention provide a biological data measurement system that is highly portable and can more accurately and non-invasively measure biological data including a blood pressure, the measurement of which is influenced by a difference between the height of a measurement site and the height of the heart (i.e., influenced by a hydrostatic pressure).

DETAILED DESCRIPTION OF EMBODIMENTS

Figure 1:
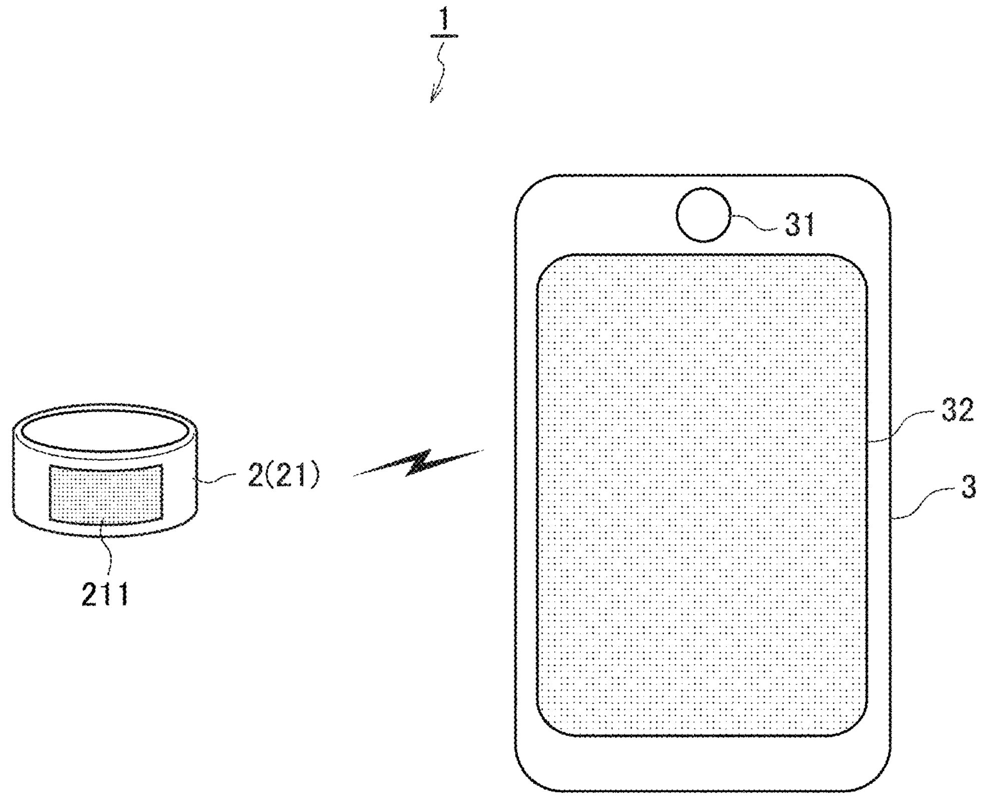
FIG. 1 is a diagram illustrating an overall configuration of a biological data measurement system according to an exemplary embodiment.

Exemplary embodiments of the present invention are described in detail below with reference to the drawings. The same reference number is assigned to the same or similar components in the drawings. Also, the same reference number is assigned to the same components in the drawings, and repeated descriptions of those components are omitted.

Figure 2:
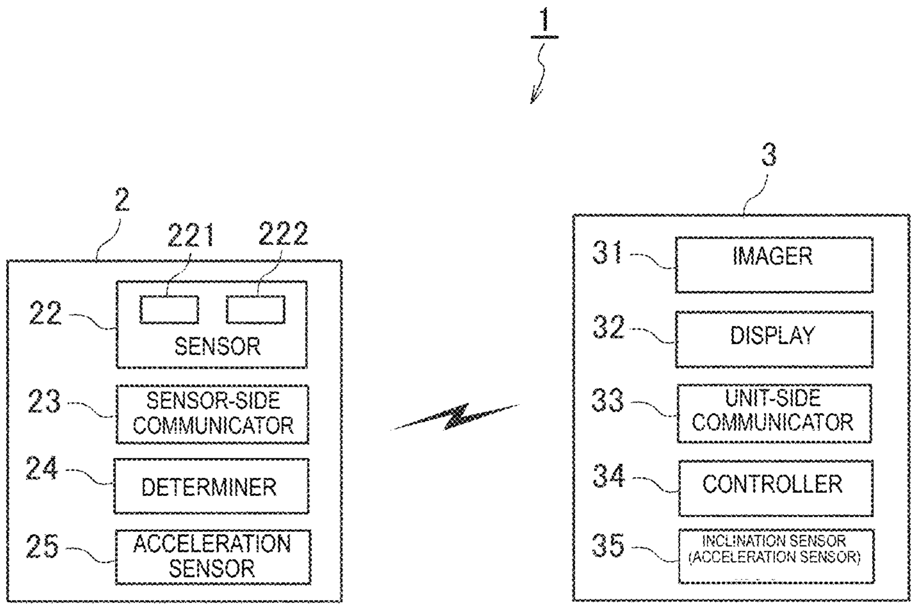
FIG. 2 is a block diagram illustrating a functional configuration of a biological data measurement system according to an exemplary embodiment.
Figure 3A:
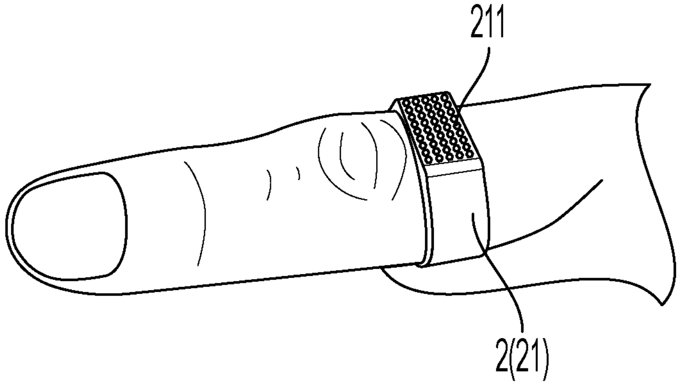
FIGS. 3(*a*) to 3(*c*) are diagrams illustrating an example of a light state variable component (light scatterer) of an annular biosensor.
Figure 3B:
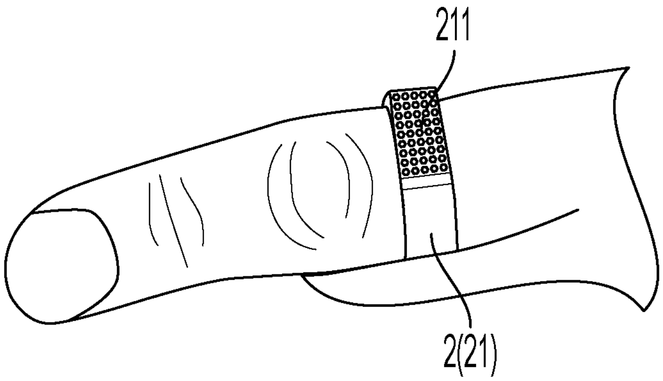
Figure 3C:
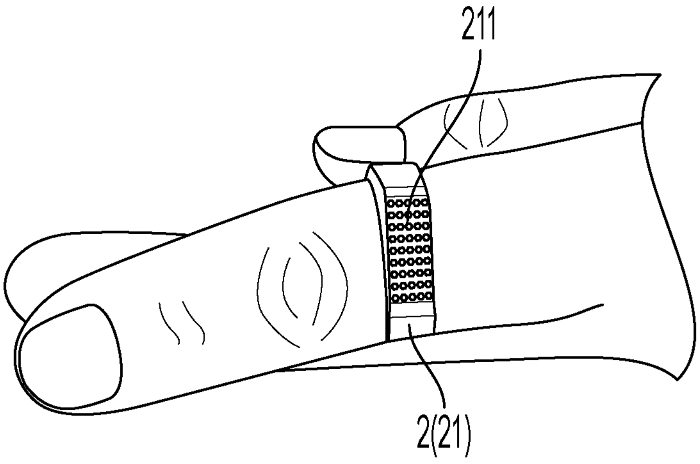
Figure 4:
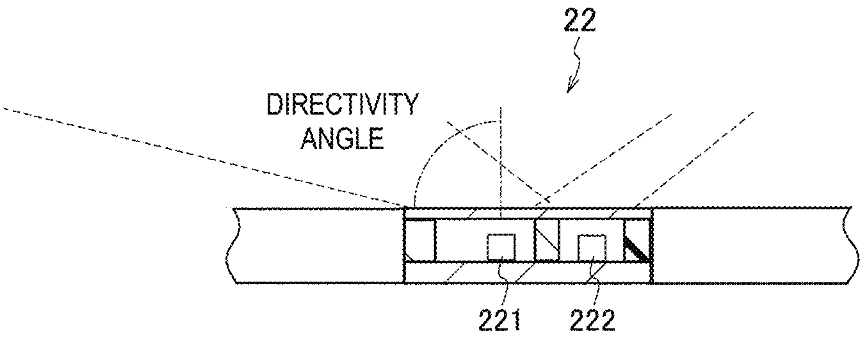
FIG. 4 is a diagram illustrating directivity angles of a light emitter (light-emitting element) and a light receiver (light-receiving element) of a photoplethysmographic sensor.

First, a configuration of a biological data measurement system 1 according to an exemplary embodiment is described with reference to FIGS. 1 through 4. FIG. 1 is a diagram illustrating an overall configuration of the biological data measurement system 1. FIG. 2 is a block diagram illustrating a functional configuration of the biological data measurement system 1. FIGS. 3(*a*)-(*c*) are diagrams illustrating an example of a light state variable component (light scatterer) 211 of an annular biosensor 2. FIG. 4 is a diagram illustrating directivity angles of a light emitter (light-emitting element) 221 and a light receiver (light-receiving element) 222 of a photoplethysmographic sensor 22.

The biological data measurement system 1 includes the annular biosensor 2 and a mobile control unit 3 that are connected via wireless communication to be able to communicate with each other. Particularly, the biological data measurement system 1 is highly portable and is configured to more accurately and non-invasively measure biological data including a blood pressure, the measurement of which is influenced by a difference between the height of a measurement site and the height of the heart (i.e., influenced by a hydrostatic pressure).

The annular biosensor 2 includes a body 21 that has an annular shape (e.g., a ring shape or a wristband shape) and is configured to be worn (i.e., is "wearable") on a hand finger or a wrist, a sensor 22 that is disposed on the inner surface of the body 21 and measures (or detects) at least a blood pressure, a sensor-side communicator 23 that transmits and receives data (e.g., measurement data and control data) to and from the mobile control unit 3, a determiner 24 that determines whether the annular biosensor 2 is worn, and an acceleration sensor 25 that detects body motion. Also, the annular biosensor 2 preferably includes a temperature sensor that detects a body surface temperature according to an exemplary aspect.

The mobile control unit 3 includes an imager 31 that is configured to capture images (still images or videos); a display 32 that is configured to prompt (or displays information prompting) a user who is holding the mobile control unit 3 in one hand (e.g., a first hand) to cause the imager 31 to capture an image of the face of the user and the other hand (e.g., the second hand) of the user wearing the annular biosensor 2 and displays the image captured by the imager 31; a unit-side communicator 33 that is configured to transmit and receive data (e.g., control data and measurement data) to and from the annular biosensor 2; a controller 34 that is configured to determine, based on the image, whether the other hand wearing the annular biosensor 2 is positioned at the height of the chest and to control the imager 31, the display 32, the unit-side communicator 33, and the annular biosensor 2 based on the result of the determination to obtain biological data (biological information) including a blood pressure; and an inclination sensor (or acceleration sensor) 35 that is configured to detect the inclination of the mobile control unit 3 with respect to the vertical direction. According to an exemplary aspect, the mobile control unit 3, which is a control terminal, is preferably implemented by, for example, a mobile terminal, such as a smartphone. In the present embodiment, a smartphone is used as the mobile control unit 3. Each of the components is described below.

The body 21 of the annular biosensor 2 has an annular shape (or a ring shape) and is wearable on a hand finger. Alternatively, the body 21 may have an annular shape (or a wristband shape) and may be wearable on a wrist. In the present embodiment, it is assumed that the annular biosensor 2 has a ring shape and is worn on a hand finger. For example, the annular biosensor 2 is worn on the index finger of one hand (e.g., the first hand or the left hand in the examples of FIGS. 5 and 6). However, the annular biosensor 2 may instead be worn on the middle finger, the ring finger, the little finger, or the thumb. The mobile control unit 3 is held in a hand (e.g., the second hand or other hand, and the right hand in the examples of FIGS. 5 and 6) different from the hand wearing the annular biosensor 2.

According to an exemplary aspect, the body 21 preferably has a shape (or an outline) that is recognizable in an image (e.g., a still image or a video) that is captured by the imager 31 of the mobile control unit 3. With this configuration, the controller 34 of the mobile control unit 3 can automatically recognize (determine) the position of the annular biosensor 2 in an image by recognizing the shape (or the outline) of the body 21 in the image. Also, with the configuration in which the body is formed to have a recognizable shape, the influence on the design (i.e., to prevent significantly damaging the design) can be reduced compared with, for example, a configuration in which a two-dimensional code is formed on the body.

Instead of, or in addition to, forming the body 21 to have a recognizable shape, a light state variable component 211 that reflects, scatters, or absorbs light so as to be recognizable in an image may be provided on the surface of the body 21. In this case, the controller 34 of the mobile control unit 3 can automatically recognize (determine) the position of the annular biosensor 2 in an image captured by the imager 31 of the mobile control unit 3 by recognizing the light state variable component 211 in the image. Also, because this configuration can be implemented by forming a light scatterer only in a portion of a mirror-finished surface of the body, the influence on the design (i.e., to prevent significantly damaging the design) can be reduced compared with, for example, a configuration in which a two-dimensional code is formed on the body.

Particularly, when a light scatterer is used, the recognition is less influenced by its orientation compared with a reflector the reflected light of which can be detected only when the reflector is oriented in a specific direction. Because the orientation of the annular biosensor 2 and the incident angle of light vary, the accuracy of image recognition can be improved by configuring the annular biosensor 2 such that the visibility of the annular biosensor 2 in an image does not greatly change.

FIG. 3(*a*) through FIG. 3(*c*) show an example of the light state variable component (light scatterer) 211 formed on the surface of the body 21. As shown in FIG. 3(*a*) through FIG. 3(*c*), there is no significant change in the visibility of the light state variable component (light scatterer) 211 in the image regardless of the incident angle of light and regardless of whether the light state variable component (light scatterer) 211 faces upward or sideways. Accordingly, the accuracy of image recognition is improved.

When light is reflected from a mirror-finished surface, the reflected light proceeds only in a fixed direction, and therefore the surface appears bright or dark depending on how the light hits the surface. However, when the body has a curved surface with, for example, a hemispherical shape, the body can be easily recognized by image recognition regardless of the incident angle of light because the light reflected from at least one position on the curved surface proceeds toward the imager 31. For example, when multiple hemispherical protrusions are arranged on the body, the array of multiple protrusions in an image can be recognized regardless of the incident angle of light. When light absorption is used, the entire surface or a part of the surface of the body 21 is formed in, for example, matte black to have a high light absorptivity (or a low light reflectance). Because the light absorptivity is high, reflected light is not detected by the imager 31 regardless of the incident angle of light, and the body can be easily recognized by image recognition. Also, to reduce false recognition, a configuration described below may be combined with the above configuration.

For example, the mobile control unit 3 may include a unit-side light emitter (implemented by the display 32 in the present embodiment) that emits light in a predetermined pattern that is recognizable in an image (or a video), and the controller 34 of the mobile control unit 3 may be configured to recognize the annular biosensor 2 reflecting or scattering the light emitted in the predetermined pattern in the image and thereby recognize (or determine) the position of the annular biosensor 2 in the image. This configuration enables the position of the annular biosensor 2 to be automatically recognized or determined even in a dark place. Also, even when there is an object reflecting illumination light or emitting light around the annular biosensor 2, the object can be distinguished from the annular biosensor 2 unless the object scatters or reflects light in synchronization with the light-emission pattern of the mobile control unit 3.

More specifically, the mobile control unit 3 includes the unit-side light emitter (the display 32), the unit-side light emitter (the display 32) emits light in a light-emission pattern (a light intensity change pattern or a hue change pattern) that is recognizable in a video captured by the imager 31, and the controller 34 recognizes the shape of the annular biosensor 2 or the light state variable component (light scatterer) 211 reflecting or scattering the light emitted in the light-emission pattern based on the captured video and determines the position of the annular biosensor 2 in the video. Here, a hue change indicates a change in color, for example, from blue to red. A hue change may also indicate a change from white (e.g., superposition of multiple wavebands) and therefore indicate a change in the wavelength of Light or an increase or a decrease in the number of wavebands of light.

For example, the display 32 of the mobile control unit 3 displays a captured video and changes the screen from the captured video to a full-screen blue display and to a full-screen red display for about 0.1 second, and the controller 34 extracts positions in the captured video where the number of blue components has increased and positions in the captured video where the number of red components has increased, identifies a portion matching the shape of the annular biosensor 2 (the body 21) or the light scatterer 211, and recognizes (or determines) the position of the annular biosensor 2. The determination of the position of the annular biosensor 2 in a dark place is normally difficult. However, this method makes it easier to determine the position of the annular biosensor 2 even in a dark place. Also, with this method, even when there is an object reflecting illumination light or emitting light around the annular biosensor 2, the object can be distinguished from the annular biosensor 2 unless the object scatters or reflects light in synchronization with the light-emission pattern of the mobile control unit 3. As another configuration, a unit-side light emitter may be provided separately from the display 32.

According to another exemplary aspect, the surface of the body 21 of the annular biosensor 2 may be provided with a letter, a symbol, a one-dimensional code (e.g., a bar code), and/or a two-dimensional code (e.g., a QR code®) that is recognizable in an image captured by the imager 31 of the mobile control unit 3. Even with this configuration, the controller 34 of the mobile control unit 3 can be configured to automatically recognize (determine) the position of the annular biosensor 2 in an image by recognizing the letter, the symbol, the one-dimensional code, and/or the two-dimensional code in the image.

Instead of the configurations described above, the annular biosensor 2 may include a sensor-side light emitter (implemented by the light-emitting element 221 of the sensor 22 in the present embodiment) that emits light in a predetermined pattern that is recognizable in an image (or a video), and the controller 34 of the mobile control unit 3 may be configured to automatically recognize (determine) the position of the annular biosensor 2 in the image by recognizing the light-emitting element 221 (the sensor-side light emitter) emitting light in the predetermined pattern based on the image. This configuration makes it possible to automatically recognize (determine) the position of the annular biosensor 2 even in a dark place. Also, even when there is an object reflecting illumination light or emitting light around the annular biosensor 2, the object can be distinguished from the annular biosensor 2 unless the object emits light in the predetermined light-emission pattern.

In this case, the sensor 22 of the annular biosensor 2 is preferably a photoplethysmographic sensor (details of which are described later) including the light-emitting element (light emitter) 221 and the light-receiving element (light receiver) 222, and the sensor-side light emitter that emits light in a predetermined pattern is implemented by the light-emitting element (light emitter) 221 including the photoplethysmographic sensor 22. In this case, as illustrated in FIG. 4, the directivity angle of the light-emitting element 221 of the photoplethysmographic sensor 22 is preferably greater than the directivity angle of the light-receiving element 222 of the photoplethysmographic sensor 22. When the directivity angle of the light-emitting element (light emitter) 221 is set at a large value, the light emitted from the light-emitting element (light emitter) 221 can more easily come out of the annular biosensor 2 and be recognized by the imager 31 (in an image). On the other hand, setting the directivity angle of the light-receiving element (light receiver) 222 at a small value reduces the entry of ambient light. As another configuration, a sensor-side light emitter may be provided separately from the light-emitting element (light emitter) 221 of the photoplethysmographic sensor 22. In this case, placing the sensor-side light emitter on the top surface (outer surface) of the annular biosensor 2 enables the imager 31 to more easily and accurately recognize (or determine) the position of the annular biosensor 2. However, this configuration increases the influence on the design of the annular biosensor 2.

More specifically, for example, when a measurement preparation command (details of which are described later) is sent from the mobile control unit 3, the annular biosensor 2 (the light-emitting element (light emitter) 221 of the photoplethysmographic sensor 22) starts emitting light in a predetermined pattern that is recognizable in a video captured by the imager 31 of the mobile control unit 3. An LED or a laser is used as the light source for the light emitter of the photoplethysmographic sensor 22; and green that is highly bioabsorbable, near infrared, or red used for a pulse oximeter is often used as the wavelength of the light emitter. However, because an optical filter corresponding to the human visual sensitivity is normally used for the imager 31 (camera), the imager 31 cannot receive near-infrared light. Also, because the light-emitting element (light emitter) 221 of the photoplethysmographic sensor 22 is disposed to face the skin of a finger when the annular biosensor 2 is worn, highly bioabsorbable green light does not pass through the finger. For the above reasons, red light is preferable in the exemplary aspect when the sensor-side light emitter is implemented by the light-emitting element (light emitter) 221 of the photoplethysmographic sensor 22.

According to an exemplary aspect, the light-emitting element (light emitter) 221 is preferably configured such that the light emitted from the light-emitting element (light emitter) 221 can easily come out of the finger and be easily recognized by the imager 31 (in an image). The angle at which the intensity of light emitted from the light-emitting element (light emitter) 221 becomes one half of the maximum intensity (normally observed at the center) is generally referred to as a directivity angle. The angle at which the sensitivity of light entering the light-receiving element (light receiver) 222 becomes one half of the maximum sensitivity (normally observed at the center) is also referred to as a directivity angle. Increasing the directivity angle of the light-emitting element (light emitter) 221 makes it easier for the light to come out of the finger. However, when the directivity angle of the light-receiving element (light receiver) 222 is increased, it becomes easier for ambient light (e.g., illumination light or sunlight) to enter the light receiver, and the noise in the photoplethysmogram increases. Therefore, the directivity angle of the light-emitting element (light emitter) 221 of the photoplethysmographic sensor 22 is preferably made greater than the directivity angle of the light-receiving element (light receiver) 222 of the photoplethysmographic sensor 22 (see FIG. 4).

On the other hand, when a sensor-side light emitter is provided separately, visible light with any wavelength may be used. Examples of light-emission patterns include a light intensity change pattern, a hue change pattern, and a mixture of these patterns. A hue change indicates a change in color, for example, from blue to red. However, a hue change does not only indicate a change in the wavelength of light but also indicates, for example, a change (an increase or a decrease in the number of wavebands of light) from white (e.g., superposition of multiple wavebands) to red. As an example, this is achieved by sequentially causing multiple LEDs with different wavelengths to emit light. Here, when the light emitter (light-emitting element) 221 of the photoplethysmographic sensor 22 is used, the hue change pattern is not suitable because only red can be suitably used as described above.

In operation in an exemplary aspect, the light intensity change pattern changes the intensity of emitted light with time. Moreover, according to an exemplary aspect, the light intensity can be changed according to a sine wave, but it is preferably changed according to a pulse wave. Moreover, the frequency of the light intensity change pattern is preferably several Hz at the highest because the light intensity change pattern needs to be captured at the frame rate of the imager 31. Also, false recognition may occur when a regular light emission cycle is used and the light emission cycle of another device is accidentally the same as the regular light emission cycle. Therefore, a special light blinking pattern is preferably used according to an exemplary aspect. For example, the pulse interval may be changed from 0.25 seconds to 0.50 seconds, to 0.75 seconds, to 0.25 seconds, to 0.50 seconds, and to 0.75 seconds to prevent false recognition. The annular biosensor 2 (the light-emitting element (light emitter) 221 of the photoplethysmographic sensor 22) continues to emit light until the annular biosensor 2 is recognized by the mobile control unit 3 and a measurement (start) command is received.

As described above, the sensor 22 is, for example, a photoplethysmographic sensor that includes the light-emitting element (light emitter) 221 and the light-receiving element (light receiver) 222 and is configured to detect a photoplethysmographic signal. The photoplethysmographic sensor optically measures, for example, a pulse by using the light absorption characteristics of hemoglobin in the blood. In the descriptions below, the sensor 22 may also be referred to as the photoplethysmographic sensor 22. As described above, in the present embodiment, the light-emitting element (light emitter) 221 also serves as the sensor-side light emitter. The sensor (photoplethysmographic sensor) 22 is disposed on the inner side of the body 21. This is because a pulse wave sensor, such as the photoplethysmographic sensor 22, can more reliably obtain a biometric signal on the ball of a finger rather than on the back of a finger.

The sensor 22 is configured to measure (or detect) at least a blood pressure. In the present embodiment, it is assumed that the sensor 22 is a blood pressure sensor that estimates a blood pressure based on a photoplethysmogram. Any known method (see, for example, Japanese Unexamined Patent Application Publication No. 2016-016295) may be used to estimate a blood pressure based on a photoplethysmogram. That is, the annular biosensor 2 is a so-called cuff-less sphygmomanometer that does not use a cuff. Any other method, such as a blood pressure estimation technique (method) using a pulse wave propagation time, may also be used.

However, regardless of the method used, an obtained blood pressure measurement may become inaccurate due to the influence of the hydrostatic pressure. To avoid the influence of the hydrostatic pressure, the blood pressure needs to be measured at or near the height of the heart of the user. When the blood pressure is measured at a position higher than the height of the heart, the measurement result becomes too low; and when the blood pressure is measured at a position lower than the height of the heart, the measurement result becomes too high. A difference of 10 cm between the blood pressure measurement position and the height of the heart causes an error of 7 to 8 mmHg in the blood pressure measurement. That is, when the blood pressure is measured on a finger with the arm hanging limply, the height difference becomes about 50 cm, which results in an error of 35 to 40 mmHg. When the blood pressure is measured by an ordinary user, who is not trained as a healthcare professional, the blood pressure is often measured at a height that is significantly different from the height of the heart of the user, and as a result, an error occurs in the blood pressure measurement. Even with a method in which the blood pressure is estimated based on a photoplethysmogram measured with a finger, it is necessary to minimize or remove the influence of a static pressure to accurately measure the blood pressure.

Also, any known method (see, for example, Japanese Patent Application No. 2017-506158) may be used to estimate a blood sugar level based on a photoplethysmogram. However, because the photoplethysmogram is influenced by the blood pressure at the time of measurement, the blood sugar level is also influenced. Therefore, even in the case of a blood sugar level sensor, it is necessary to take an appropriate measurement posture to limit the influence of the blood pressure. The blood pressure may increase in a posture, such as a stooping posture, in which pressure is applied to the abdomen, and the pulse and breathing may also change depending on the posture. Accordingly, it is necessary to take an appropriate measurement posture. A photoplethysmogram includes information on vascular resistance. Because a photoplethysmogram is influenced by the blood pressure, measuring the vascular resistance at the height of the heart reduces variation in the measurement. Although the vascular resistance is used as an example, the same also applies to the estimation of the blood flow rate, the blood sugar level, and the degree of arteriosclerosis based on waveforms. Also, because the measurement posture influences the pulse rate, the blood flow rate, the body surface temperature, and the breathing, measurement variation can be reduced by performing measurement in a fixed posture. Examples of biological data (biological information) to be measured may include, in addition to a blood pressure, a pulse wave, a pulse, oxygen saturation, a blood sugar level, a body surface temperature, an activity amount, vascular resistance, a blood flow rate, the degree of arteriosclerosis, and breathing. Measuring multiple types of biological data (information) at the same time enables physical conditions and signs of diseases to be estimated.

The sensor-side communicator 23 is configured to transmit and receive data (e.g., measurement data and control data) to and from the mobile control unit 3. Here, in the present embodiment, Bluetooth® is adopted as a radio communication standard in the exemplary aspect. That is, the sensor-side communicator 23 has transmission and reception functions that are based on Bluetooth®. The radio communication standard to be used is not limited to Bluetooth®, and any other standard may also be used. More specifically, the sensor-side communicator 23 determines whether the annular biosensor 2 is connected to the mobile control unit 3. Also, the sensor-side communicator 23 transmits wearing state information (details of which are described later) of the annular biosensor 2 to the mobile control unit 3. Also, the sensor-side communicator 23 receives a measurement preparation command and a measurement (start) command transmitted from the mobile control unit 3. The sensor-side communicator 23 transmits obtained biological data, such as a blood pressure, to the mobile control unit 3 (at a predetermined timing (or interval)).

The determiner 24 is configured to determine whether the annular biosensor 2 is worn on a hand finger (or on a wrist). When posture determination (details of which are described later) is performed while the annular biosensor 2 is not worn, it may be mistakenly determined that the posture is appropriate even though the posture is not appropriate. This problem can be avoided by performing posture determination only when the annular biosensor 2 is worn.

Whether the annular biosensor 2 is worn can be determined based on whether a pulse wave is detected by the photoplethysmographic sensor 22. This method reduces the possibility that the annular biosensor 2 is determined to be worn on a finger even though the annular biosensor 2 is not worn on a finger. However, because it is necessary to measure two or more beats to detect a pulse wave, detecting a pulse wave may take three or more seconds. Therefore, whether the annular biosensor 2 is worn may be determined based on whether the intensity of light received by the photoplethysmographic sensor 22 has exceeded a threshold. When the photoplethysmographic sensor 22 is a reflective sensor, the received light intensity becomes low when the annular biosensor 2 is not worn. In this case, when the received light intensity becomes less than a threshold, it is determined that the annular biosensor 2 is not worn. When the photoplethysmographic sensor 22 is a transmission sensor, the received light intensity becomes high when the annular biosensor 2 is not worn. In this case, when the received light intensity becomes greater than a threshold, it is determined that the annular biosensor 2 is not worn. This method enables quick determination. With this method, however, it may be determined (i.e., misjudged) that the annular biosensor 2 is worn when any object that blocks light is inserted into the annular biosensor 2. Therefore, whether the annular biosensor 2 is worn on a finger may be determined by combining the above method with another method such as a method in which the annular biosensor 2 is determined to be not worn when no movement is detected by, for example, the acceleration sensor 25 or a gyro sensor or a method in which the annular biosensor 2 is determined to be not worn when a temperature detected by a temperature sensor for detecting a body surface temperature is less than or equal to a predetermined value.

The result of determination by the determiner 24 is transmitted by the sensor-side communicator 23 to the mobile control unit 3. Also, the sensor-side communicator 23 of the annular biosensor 2 transmits, to the mobile control unit 3, the result of determining whether the annular biosensor 2 is worn on a hand finger or a wrist. The controller 34 of the mobile control unit 3 prevents determination of inclination of the trunk of the user (posture determination, details of which are described later) when the annular biosensor 2 is not worn on a hand finger nor on a wrist.

The acceleration sensor 25 is configured to detect the acceleration of the annular biosensor 2, i.e., the body motion of the user wearing the annular biosensor 2. The result of detection by the acceleration sensor 25 is also transmitted by the sensor-side communicator 23 to the mobile control unit 3.

Figures 5A, 5B, 5C:
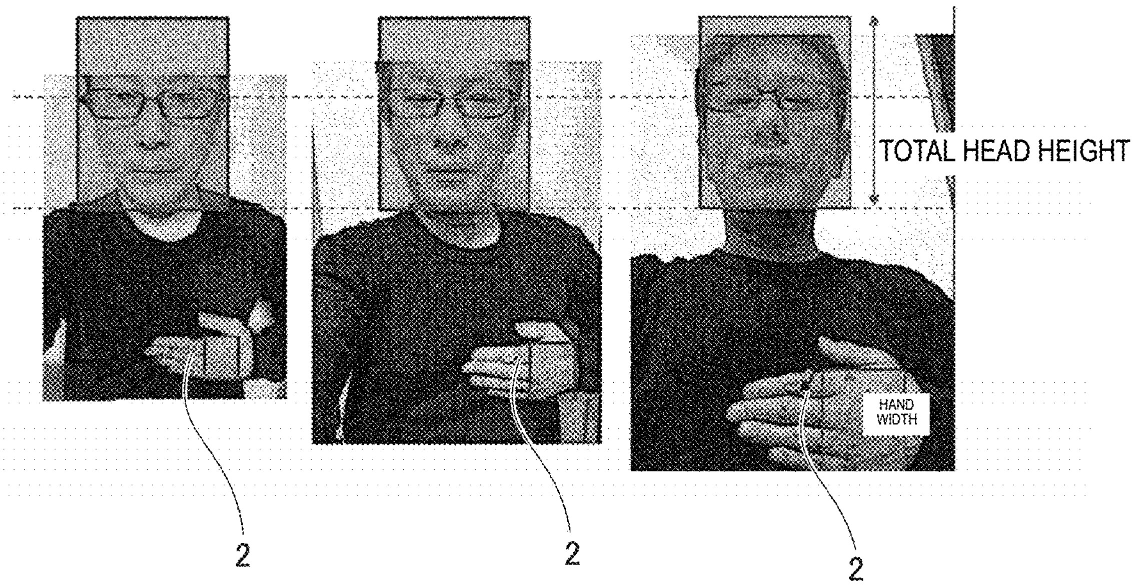
FIGS. 5(*a*) to 5(*c*) are diagrams showing examples of captured images of a user including an image 5(*a*) captured from above, an image 5(*b*) captured from the front, and an image 5(*c*) captured from below.
Figure 6:
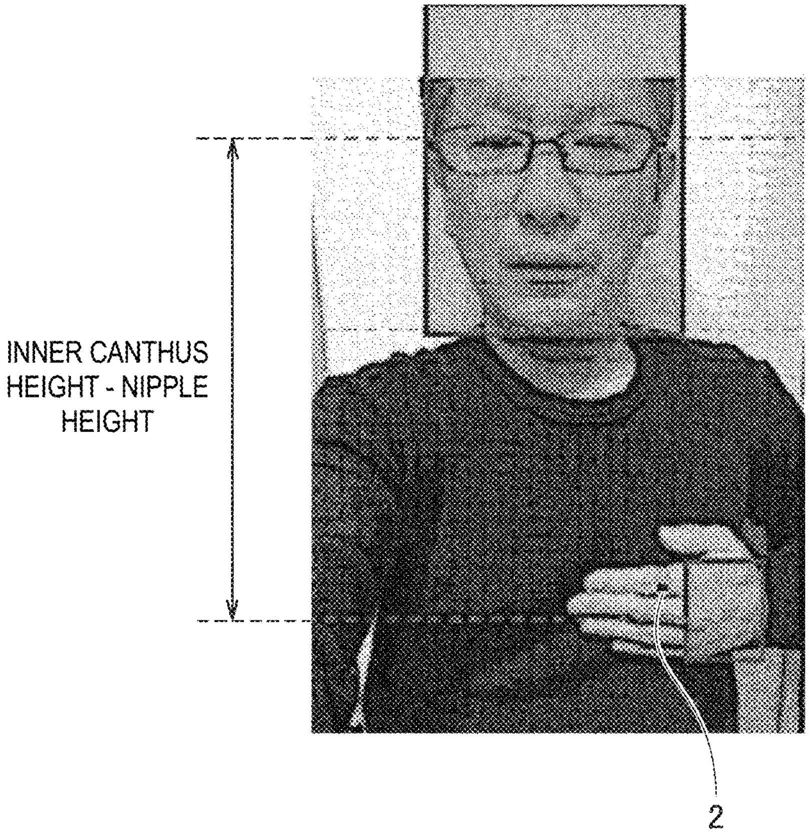
FIG. 6 is a diagram for describing a method of estimating the height of the chest (heart).

The imager (camera) 31 of the mobile control unit 3 is configured to capture an image (e.g., a still image or a video). The imager 31 is disposed on a side of the mobile control unit 3 on which the display 32 is provided. As illustrated in FIGS. 5 and 6, when the user places one hand (e.g., the left hand) wearing the annular biosensor 2 on the chest (so as to cover a nipple) and holds the mobile control unit 3 in the other (opposite) hand (e.g., the right hand), the imager 31 captures an image of the face of the user and the hand placed on the chest.

According to an exemplary aspect, the display 32 is implemented by, for example, an LCD display. The display 32 displays (or presents), for example, images or information as described in (1) through (7) below.

(1) The display 32 prompts (or displays information prompting) the user holding the mobile control unit 3 in one hand to place the other hand wearing the annular biosensor 2 on the chest.

(2) The display 32 prompts (or displays information prompting) the user to cause the imager 31 to capture an image such that the face of the user and the other hand of the user wearing the annular biosensor 2 fit in a frame.

(3) The display 32 displays, in real time, the image (e.g., a still image or a video) captured by the imager 31. The display 32 also graphically displays (or presents) a display position of the face and a recommended range of the display size of the face. More specifically, the display 32 superimposes a substantially oval or rectangular figure representing the appropriate position and size of the face on the image. Graphically displaying the appropriate range of the display position of the face and the display size of the face on the display 32 makes it easier for the user to recognize the appropriate range. This in turn enables the user to easily correct the position and size of the displayed face.

(4) When the face of the user in the image is recognized by the controller 34 of the mobile control unit 3, the display 32 informs (or displays information indicating) whether the display position of the face and the display size of the face are within a recommended range. Thus, because both of the actual position and size of the face in an image and the appropriate range of the position and size of the face are displayed, the user can easily make a correction. Here, it is desirable to determine the height of the face based on the eye height, such that the estimation accuracy of the relative position between the face and the heart can be improved by automatically recognizing the eye position during the automatic recognition of the face.

(5) The display 32 displays (or presents) an image such that the trunk of the user is oriented in the vertical direction and prompts the user to make adjustments. More specifically, the display 32 presents (or displays) information indicating whether the relative position between the mobile control unit 3 and the trunk of the user and the inclination of the trunk of the user with respect to the vertical direction are within predetermined ranges. As a result, the user can be informed as to whether the relative position between the mobile control unit 3 and the trunk and the inclination of the trunk are within appropriate ranges and thereby enables the user to determine whether the relative position and the inclination of the trunk are out of the appropriate ranges and to easily make corrections.

(6) The display 32 prompts (or displays information prompting) the user to make adjustments such that the hand wearing the annular biosensor 2 is positioned at the height of the chest of the user.

(7) As described above, the display 32 may also serve as the unit-side light emitter in an exemplary aspect. Because the configuration in which the display 32 also serves as the unit-side light emitter is described above, detailed descriptions of this configuration are omitted here.

The unit-side communicator 33 is configured to transmit and receive data (e.g., control data (commands) and measurement data) to and from the annular biosensor 2 (the sensor-side communicator 23). More specifically, the unit-side communicator 33 determines whether the unit-side communicator 33 is connected to the sensor-side communicator 23 via Bluetooth®. Also, the unit-side communicator 33 transmits a measurement preparation command and a measurement (start) command to the sensor-side communicator 23. The unit-side communicator 33 receives wearing state information transmitted from the annular biosensor 2. The unit-side communicator 33 also receives biological data, such as a blood pressure, transmitted from the annular biosensor 2.

The controller 34 is configured to estimate the difference in height between the hand and the heart according to steps (1) through (4) below. Details of each step are described later.

(1) The controller 34 obtains the relative position between the mobile control unit 3 and the trunk based on the ratio between the sizes of the face and the hand in an image.

(2) The controller 34 obtains the inclination of the trunk based on the inclination of the mobile control unit 3 and the relative position between the mobile control unit 3 and the trunk obtained in (1).

(3) The controller 34 statistically determines the difference in height between the face and the heart, and obtains the height of the heart in the image based on the difference, the relative position between the mobile control unit 3 and the trunk obtained in (1), and the inclination of the trunk obtained in (2).

(4) The controller 34 obtains the difference in height between the hand and the heart.

(5) Moreover, in an exemplary aspect, the controller 34 can further determine the position of the annular biosensor 2 to increase the accuracy of the difference in height between the hand and the heart obtained in (4).

The controller 34 determines, based on an image (e.g., a still image or a video), whether the other hand wearing the annular biosensor 2 is positioned at the height of the chest and controls the imager 31, the display 32, the unit-side communicator 33, and the annular biosensor 2 based on the result of the determination to obtain biological data (or biological information) including a blood pressure. For this purpose, the controller 34 includes a microprocessor that is configured to perform calculations, an EEPROM that stores, for example, a program for causing the microprocessor to perform various processes, a RAM that temporarily stores data, and an external interface (I/F). According to an exemplary aspect, functions and operations of the controller 34 can be implemented by executing a program stored in, for example, the EEPROM by the microprocessor.

Moreover, the controller 34 is configured to estimate the relative position between the face and the chest (or the heart) based on the size of the face in an image. More specifically, the controller 34 automatically recognizes the face of the user in an image and estimates the position of the chest (or the heart) of the user in the image based on the display position and the display size of the face. Because the distance between the face and the heart can be estimated based on the size of the face, the accuracy of determining whether the annular biosensor 2 is at the height of the chest can be improved.

In this process, the controller 34 statistically estimates the relative position between the face and the heart based on physical information such as a body height. That is, the controller 34 obtains prestored physical information of the user and estimates the position of the chest (or the heart) of the user by taking into account (referring to) the physical information. For example, this makes it possible to estimate the size of the face and the distance between the face and the heart based on the body height (and the weight) and thereby the accuracy of determining whether the annular biosensor 2 is at the height of the chest can be improved.

However, because the relative position changes in a posture, such as a stooping posture, in which the trunk is greatly bent, it is assumed here that the user is in a seated position and the trunk is not tilted. For example, because "AIST anthropometric database 1991-1992" does not include data related to the height of the heart, nipple height data is used as a substitute in the present embodiment. The difference in height between the face and the heart can be statistically obtained by using B2 Entocanthion height–B6 Nipple height as a substitute. The controller 34 estimates the difference between, for example, the eye (entocanthion height) and the nipple (nipple height) by referring to statistical data based on the size (total head height) of the face in an image. Instead of the total head height, A2 Head breadth, A3 Bitragion breadth, or A4 Ear to ear breadth may be used. This is because there is a case where the vertex sticks out of the frame and a case where it is difficult to recognize the vertex by image recognition due to the hair style. In such a case, the estimation accuracy can be improved by using the height information of the user. When the height information of the user is not available, estimation may be performed using ratios of average values of statistics. The controller 34 may read physical information (e.g., a body height) of the user that is input by the user beforehand using the mobile control unit 3 and stored in a memory or a server or may read data that indicates, for example, results of a medical examination and is stored in a server.

Examples of lengths used as hand sizes include a hand length, a dorsal finger length, and a hand breadth (see "AIST Japanese hand dimensions data"). Although it is possible to use, for example, a finger width, the finger width is often influenced by a body fat percentage, and the estimation accuracy may decrease when the hand size is estimated based only on a body height. Among the hand sizes described above, the estimation accuracy using the hand length may decrease when the wrist is covered by a sleeve. Also, the estimation accuracy using the dorsal finger length may decrease when the finger is bent. When using a dorsal finger length, the dorsal finger length of the thumb (first finger), which is not easily bent, is most suitable. The hand breadth is suitable as a length indicating the hand size.

As described above, the blood pressure varies depending on the difference in height between the measurement site and the heart. When the measurement sight is higher than the heart by 10 cm, the blood pressure decreases by 7 to 8 mmHg. Accordingly, it is important to perform measurement by placing the measurement site at the same height as the heart. In general, the blood pressure deviates from the true value as the difference between the height of the annular biosensor 2 and the height of the heart increases. Therefore, it is possible to determine whether the measured blood pressure differs from the true value by determining the difference in height. Moreover, the inclination of the trunk with respect to the vertical direction may become a factor that causes the estimated heights of the face and the heart to become inaccurate. It is possible to determine whether the measured blood pressure is different from the true value by determining whether the inclination is out of a predetermined range.

Figure 7A:
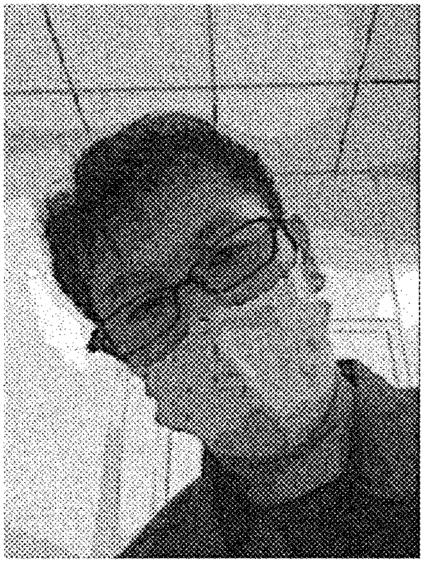
FIGS. 7(*a*) and 7(*b*) are diagrams showing examples of images including an image 7 (*a*) in which only the trunk is tilted to the right and an image 7(*b*) in which the trunk and a mobile control unit are equally tilted to the right.
Figure 7B:
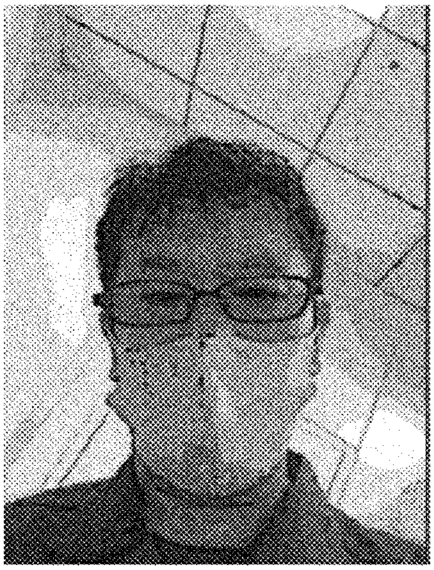

According to an exemplary aspect, the inclination of the trunk of the user in the lateral direction can be estimated based on the inclination of the face in an image in the lateral direction and the inclination of the mobile control unit 3 in the lateral direction. When the inclination in the lateral direction exceeds a predetermined range, the user is notified via, for example, the display 32. Here, FIG. 7(*a*) is an example of an image in which only the trunk is tilted to the right. Also, FIG. 7(*b*) is an example of an image in which the trunk and the mobile control unit 3 are equally tilted to the right.

The mobile control unit 3 includes the inclination sensor (or acceleration sensor) 35 that is configured to detect the inclination of the mobile control unit 3 with respect to the vertical direction. The controller 34 determines whether the inclination of the trunk of the user with respect to the vertical direction and the lateral direction is within a predetermined range based on the inclination of the mobile control unit 3 with respect to the vertical direction detected by the inclination sensor 35.

Also, the controller 34 is configured to estimate the inclination of the trunk of the user in the forward-backward direction based on the display size of the face and the display size of the hand in an image. For example, the controller 34 statistically estimates the ratio between the size of the face and the size of the hand based on, for example, the height information of the user. More specifically, the controller 34 estimates the size of the face and the size of the hand based on, for example, height information and calculates the ratio (which is referred to as an actual ratio) between the size of the face and the size of the hand. The controller 34 also obtains the sizes of the face and the hand in the image and calculates the ratio (which is referred to as an intra-image ratio) between the sizes of the face and the hand. Then, the controller 34 estimates the relative position between the mobile control unit 3 and the trunk based on whether the intra-image ratio is within a predetermined range with respect to the actual ratio and thereby determines whether the relative position between the mobile control unit 3 and the trunk is within a predetermined range. In this case, because the sizes of the face and the hand can be statistically estimated based on the body height (and the weight), the relative position between the mobile control unit 3 and the trunk can be estimated by automatically recognizing the face and the hand in the image and calculating the ratio between the sizes of the face and the hand in the image.

Here, FIGS. 5(*a*) to 5(*c*) show examples of images that are captured while moving the mobile control unit 3 (the imager 31) up and down. From the left, the image in FIG. 5(*a*) is captured from above, the image FIG. 5(*b*) is captured from the front, and the image FIG. 5(*c*) is captured from below. As shown, the hand breadth varies when the size of the face is kept constant. The values of the ratio "hand breadth/total head height" estimated based on the images are as follows: 0.22 (above), 0.30 (front), and 0.54 (below). The ratio "hand breadth/total head height" calculated based on average values of young adult males in the statistical data is 0.35 that is close to the value calculated based on the front image. When the ratio "hand breadth/total head height" is calculated based on an assumption that all data items in the database are normally distributed and the position of the body height of the user in the normal distribution is the same as the positions of other data items, the ratio becomes 0.34 and is closer to the value calculated based on the front image.

When p indicates an average of statistics and σ indicates the standard deviation, the body height of the user is represented by formula (1) below using the statistics μ of the body height and σ; and the total head height and the hand breadth of the user are estimated based on an obtained coefficient "a" and the statistics of the total head height and the hand breadth.

$$\text{User measurement value} = \mu i + a \times \sigma i \quad (1)$$

Accordingly, the relative position between the trunk and the mobile control unit 3 can be estimated by determining the hand breadth and the total head height by image recognition. Then, the user is prompted to adjust the height of the mobile control unit 3 such that the mobile control unit 3 becomes approximately parallel to the trunk (to be able to capture an image from the front). Also, the estimation accuracy can be improved by using the height information of the user.

Next, the controller 34 is configured to estimate whether the trunk is tilted forward or backward based on the inclination of the mobile control unit 3. As described above, because the relative position between the mobile control unit 3 and the trunk has already been determined (the mobile control unit 3 is parallel to the trunk), the inclination of the trunk in the forward-backward direction can be estimated by measuring the inclination of the mobile control unit 3 with the inclination sensor 35 built in the mobile control unit 3. Accordingly, the controller 34 recognizes the face of the user and the hand wearing the annular biosensor 2 based on an image, estimates the relative position between the mobile control unit 3 and the trunk of the user based on the display size of the face of the user and the display size of the hand, and determines whether the inclination of the trunk of the user with respect to the vertical direction and the forward-backward direction is within a predetermined range based on the inclination of the mobile control unit 3 detected by the inclination sensor (or acceleration sensor) 35 and the relative position between the mobile control unit 3 and the trunk of the user. Here, even when the relative position between the mobile control unit 3 and the trunk is within the predetermined range, the accuracy of determination of the chest height decreases if the inclination of the trunk with respect to the vertical direction is large. Accordingly, the accuracy of determination of the chest height can be determined by determining whether the inclination of the trunk with respect to the vertical direction is within a predetermined range based on the inclination of the mobile control unit 3.

When the user is stooping or leaning backward (e.g., retroverted), the height relationship between the face and the heart changes, the estimated height of the heart becomes lower than the actual height of the heart, and, as a result, the accuracy of the measurement of the blood pressure decreases. Also, the blood pressure may increase in a posture, such as a stooping posture, in which pressure is applied to the abdomen. However, it is difficult for the user to notice such stooping and backward-leaning postures by him/herself. By determining the inclination of the trunk with respect to the vertical direction, the user can be informed that the user is stooping or leaning backward and thereby request the user to correct the posture.

After determining the hand breadth and the total head height by image recognition and estimating the relative position between the trunk and the mobile control unit 3, instead of (or in addition to) prompting the user to adjust the height of the mobile control unit 3 such that the mobile control unit 3 becomes approximately parallel to the trunk (to be able to capture an image from the front), the relative inclination between the mobile control unit 3 and the trunk may be estimated based on the intra-image ratio between the hand breadth and the total head height, and the inclination of the trunk with respect to the vertical direction may be obtained together with the inclination of the mobile control unit 3 with respect to the vertical direction. By determining whether the inclination of the trunk with respect to the vertical direction is out of the predetermined range, it is possible to determine whether a measured blood pressure differs from the true value.

As described above, the controller 34 is configured to recognize, based on an image (e.g., a still image or a video), the face of the user and the hand wearing the annular biosensor 2, estimate the relative position between the mobile control unit 3 and the trunk of the user based on the display size of the face of the user and the display size of the hand, determine whether the inclination of the trunk of the user with respect to the vertical direction is within a predetermined range based on the result of the estimation (the relative position between the mobile control unit 3 and the trunk of the user) and the inclination of the mobile control unit 3 detected by the inclination sensor 35, and control the annular biosensor 2 based on the result of the determination. Because the size of the face and the size of the hand can be statistically estimated based on the body height (and the weight), the relative position (or inclination) between the mobile control unit 3 and the trunk can be estimated by automatically recognizing the face and the hand in the image. Moreover, the inclination of the trunk with respect to the vertical direction can be estimated by adjusting the inclination of the mobile control unit 3 to match the inclination of the trunk, and whether the measured blood pressure is different from the true value can be determined by determining whether the inclination of the trunk is out of the predetermined range.

Figure 8B:
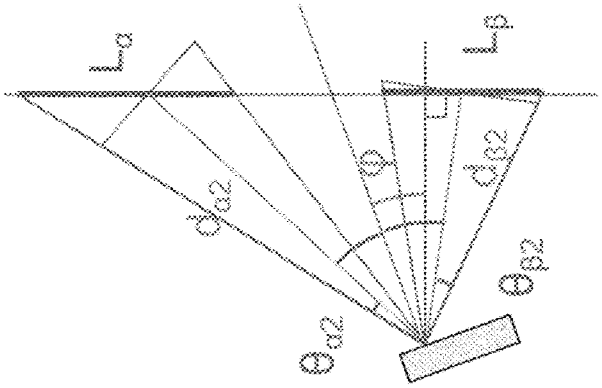
FIGS. 8(*a*) and 8(*b*) are diagrams for describing how the intra-image ratio between a hand breadth and a total head height changes depending on the orientation of an imager (camera).
Figure 8A:
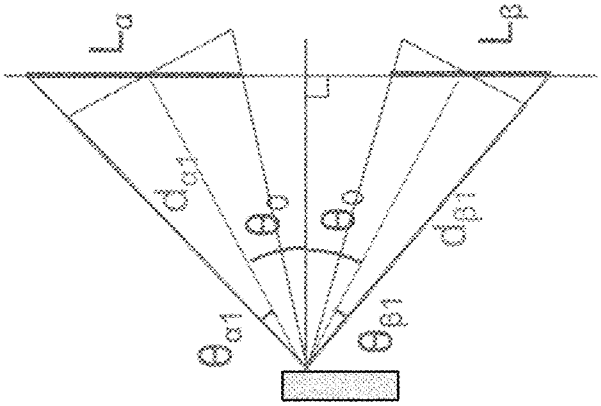

With reference to FIGS. 8(*a*) and 8(*b*), how the intra-image ratio between the hand breadth and the total head height changes depending on the orientation of the imager 31 is described using a model. In particular, FIG. 8(*a*) illustrates a case where the orientation of the imager 31 is perpendicular to a straight line on which α (face) and β (hand) are placed, and FIG. 8(*b*) illustrates a case where the orientation of the imager 31 is tilted by an angle σ from the state illustrated in FIG. 8(*a*). As shown, the total head height and the hand breadth are represented, respectively, by a straight line α with a length Lα and a straight line β with a length Lβ that are on the same straight line. The depth is omitted to simplify descriptions. When the imager 31 is oriented perpendicular to the straight line, on which α and β are placed so that α and β are located in the same position in the lateral direction in a captured image, dα1 and dβ1 indicate the distance between the imager 31 and α and the distance between the imager 31 and β, respectively, and θ0 and −θ0 indicate angles with respect to the direction in which the imager 31 is oriented. Also, θα1 and θβ1 indicate halves of the corresponding angle ranges in which α and β can be captured by the imager 31. Here, formula (2) below holds.

$$D\alpha 1 = d\beta 1 = d0 \quad (2)$$

Based on FIG. 8(*a*), formulas (3) and (4) below are obtained.

$$D\alpha 1\ \tan(\theta\alpha 1) = L\alpha\ \cos(\sigma 0) \quad (3)$$

$$d\beta 1\ \tan(\theta\beta 1) = L\beta\ \cos(\theta 0) \quad (4)$$

Accordingly, formula (5) below holds.

$$L\beta/L\alpha = d\beta 1/d\alpha 1 \times (\tan(\theta\beta 1)/\tan(\theta\alpha 1)) = \mathrm{Tan}(\theta\beta 1)/\tan(\theta\alpha 1) \quad (5)$$

Here, Lβ/Lα indicates an actual ratio, tan(θB1)/tan(θα1) indicates an intra-image ratio, and in this case, Lβ/Lα and tan(θβ1)/tan(θα1) match each other.

FIG. 8(*b*) illustrates a case where the imager 31 is tilted upward by the angle φ. Here, it is assumed that the positions (θ0 and −θ0) of α and β in the image do not change. The angles are in ranges that satisfy formulas (6) below.

$$0° < \theta 0 < 90°, 0° < \theta 0 + \varphi < 90°, 0° < \theta 0 - \varphi < 90° \quad (6)$$

Based on FIG. 8(*b*), formulas (7) to (9) hold.

$$D\alpha 2\ \tan(\theta\alpha 2) = L\alpha\ \cos(\theta 0 + \varphi) \quad (7)$$

$$d\beta 2\ \tan(\theta(\theta\beta 2) = L\beta\ \cos(\theta 0 - \varphi) \quad (8)$$

$$d\alpha 2\ \cos(\theta 0 + \varphi) = d\beta 2\ \cos(\theta 0 - \varphi) \quad (9)$$

Accordingly, formula (10) below holds.

$$D\beta 2/d\alpha 2 = \cos(\theta 0 + \varphi)/\cos(\theta 0 - \varphi) \quad (10)$$

Moreover, Lβ/Lα is obtained in the same manner as described above.

$$L\beta/L\alpha = d\beta 2\ \tan(\theta\beta 2)/\cos(\theta 0 - \varphi)/(d\alpha 2\ \tan(\theta\alpha 2)/\cos(\theta 0 + \varphi)) = \tan(\theta\beta 2)/\tan(\theta\alpha 2) \times (d\beta 2/d\alpha 2) \times (\cos(\theta 0 + \varphi)/\cos(\theta 0 - \varphi)) = \tan(\theta\beta 2)/\tan(\theta\alpha 2) \times (\cos(\theta 0 + \varphi)/\cos(\theta 0 - \varphi))\hat{}2 \quad (11)$$

Accordingly, formula (12) below holds.

$$\mathrm{Tan}(\theta\beta 2)/\tan(\theta\alpha 2) = L\beta/L\alpha \times (\cos(\theta 0 - \varphi)/\cos(\theta 0 + \varphi))\hat{}2 \quad (12)$$

Here, tan(θβ2)/tan(θα2) is an intra-image ratio and changes from the actual ratio Lβ/Lα by (cos(θ0−φ)/cos(θ0+φ))^2. Here, when φ>0°, formula (13) below holds.

$$0° < \theta 0 - \varphi < \theta 0 + \varphi < 90° \quad (13)$$

That is, formula (14) below holds.

$$\mathrm{Cos}(\theta 0 - \varphi) > \cos(\theta 0 + \varphi) \quad (14)$$

Accordingly, the intra-image ratio becomes greater than the actual ratio.

When φ<0° (when the imager 31 is tilted downward), formula (15) below holds.

$$0° < \theta 0 + \varphi < \theta 0 - \varphi < 90° \quad (15)$$

That is, formula (16) below holds.

$$\mathrm{Cos}(\theta 0 - \varphi) < \cos(\theta 0 + \varphi) \quad (16).$$

Accordingly, the intra-image ratio becomes less than the actual ratio.

After estimating the actual ratio Lβ/Lα based on the statistical data, (cos(θ0−φ)/cos(θ0+φ))^2 is calculated based on the ratio between the actual ratio and the intra-image ratio to estimate the angle φ. Based on the angle φ, the relative inclination between the imager 31 (the mobile control unit 3) and the trunk can be obtained. The inclination of the trunk with respect to the vertical direction can be obtained by obtaining the inclination of the imager 31 (e.g., the mobile control unit 3) with respect to the vertical direction by using the built-in inclination sensor 35. By determining whether the inclination of the trunk with respect to the vertical direction is out of the predetermined range, it is possible to determine whether a measured blood pressure differs from the true value.

After the relative position between the mobile control unit 3 and the trunk and the inclination of the mobile control unit 3 are determined, the controller 34 can be configured to estimate the height of the heart. The height of the heart may be substituted by, for example, the nipple height. The height of the heart is estimated based on the position of the eye in the image and the value of "entocanthion height−nipple height" in the database. In the image of FIG. 6, it is estimated that the heart is approximately at the position of the middle finger. When the nipple is covered with the palm, the middle finger tends to be placed approximately at the height of the nipple, and therefore the height of the heart can be accurately estimated. In the present embodiment, estimation is performed using publicly available anthropometric data. However, estimation may also be performed based on anthropometric data obtained separately or based on measurements of the user that are obtained and entered.

With the configuration described above, it is possible to determine that the user is in an appropriate measurement posture (e.g., not stooping nor leaning backward) and that the hand wearing the annular biosensor 2 is at the height of the nipple. Accordingly, if the position of the annular biosensor 2 in an image can be determined, the difference in height between the annular biosensor 2 and the heart can be estimated. The method of determining the position of the annular biosensor 2 in an image is described above, and detailed descriptions of the method are omitted here.

As described above, it is important to measure the blood pressure at the height of the heart at rest, and an accurate blood pressure cannot be measured unless the user is in an appropriate posture. On the other hand, measuring the blood pressure at the height of the heart limits (restricts) the measurement posture of the user and may be difficult when data needs to be obtained continuously or regularly. Therefore, it is important to calculate the reliability level of a measured value and to correct a measured value to substantially match the blood pressure measured in an approximate measurement posture. The measured blood pressure becomes more inaccurate as the posture deviates from the appropriate posture. Therefore, the user is preferably enabled to handle a measured blood pressure taking into account the risk that the measured blood pressure is different from the true value by calculating the reliability level of the measured blood pressure according to the deviation of the posture from the appropriate posture.

For this purpose, the controller 34 can be configured to calculate (obtain) a reliability level of biological data including a (measured) blood pressure based on the result (posture determination result) of determining the inclination of the trunk of the user. Here, it is important to measure the blood pressure at the height of the heart at rest, and an accurate blood pressure cannot be measured unless the user is in an appropriate posture. The measured blood pressure becomes more inaccurate as the posture deviates from the appropriate posture. However, it is possible to handle a measured blood pressure taking into account the risk that the measured blood pressure is different from the true value by calculating the reliability level of the measured blood pressure.

Also, the convenience for the user can be improved by correcting a measured blood pressure to substantially match the blood pressure measured in an appropriate measurement posture. If the absolute positions of the face and the mobile control unit 3 can be estimated, the difference in height between the annular biosensor 2 and the heart can be estimated. The measured blood pressure may be corrected by an amount corresponding to the difference in height. The controller 34 can be configured to also correct biological data, such as a blood pressure, based on the result (posture determination result) of determining the inclination of the trunk of the user. For example, because the blood pressure increases in a stooping posture, a blood pressure estimated in a stooping posture may be decreased based on data including inclinations of the trunk and blood pressure values obtained beforehand.

The blood pressure can be corrected if the difference in height between the annular biosensor 2 and the chest can be estimated. However, the blood pressure estimation can be performed more accurately when the annular biosensor 2 is placed at the height of (or perpendicular to) the chest. That is, the blood pressure accuracy can be made more stable by measuring the blood pressure each time at the height of the heart compared with cases where the blood pressure is measured at positions lower and higher than the heart. However, measuring the blood pressure at the height of the heart limits (restricts) the measurement posture of the user and may be difficult (may inflict suffering on the user) when data needs to be obtained continuously or regularly. Therefore, when continuously or regularly obtaining data, the measured blood pressure may be corrected to substantially match the blood pressure measured in an appropriate measurement posture.

Figure 9:
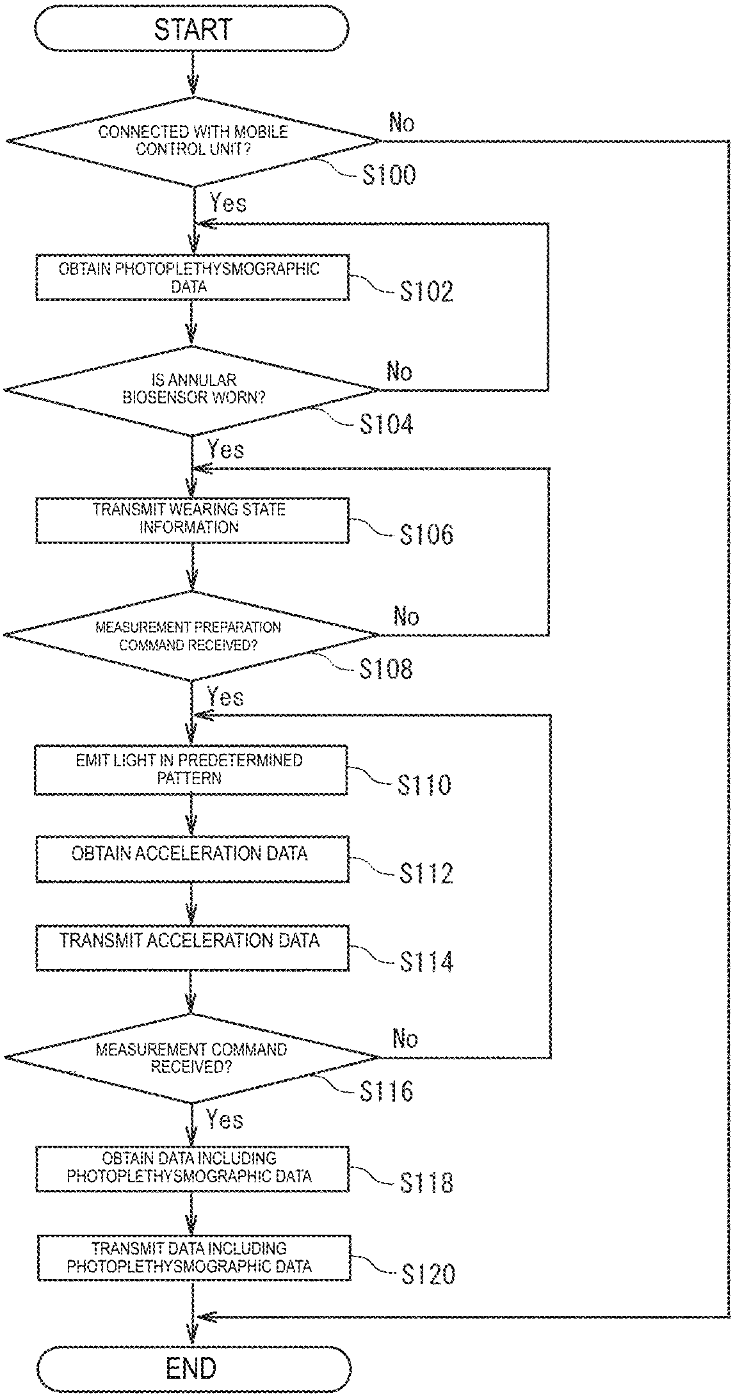
FIG. 9 is a flowchart illustrating a process of measuring, for example, a blood pressure performed by an annular biosensor that includes a biological data measurement system according to an exemplary embodiment.
Figure 10:
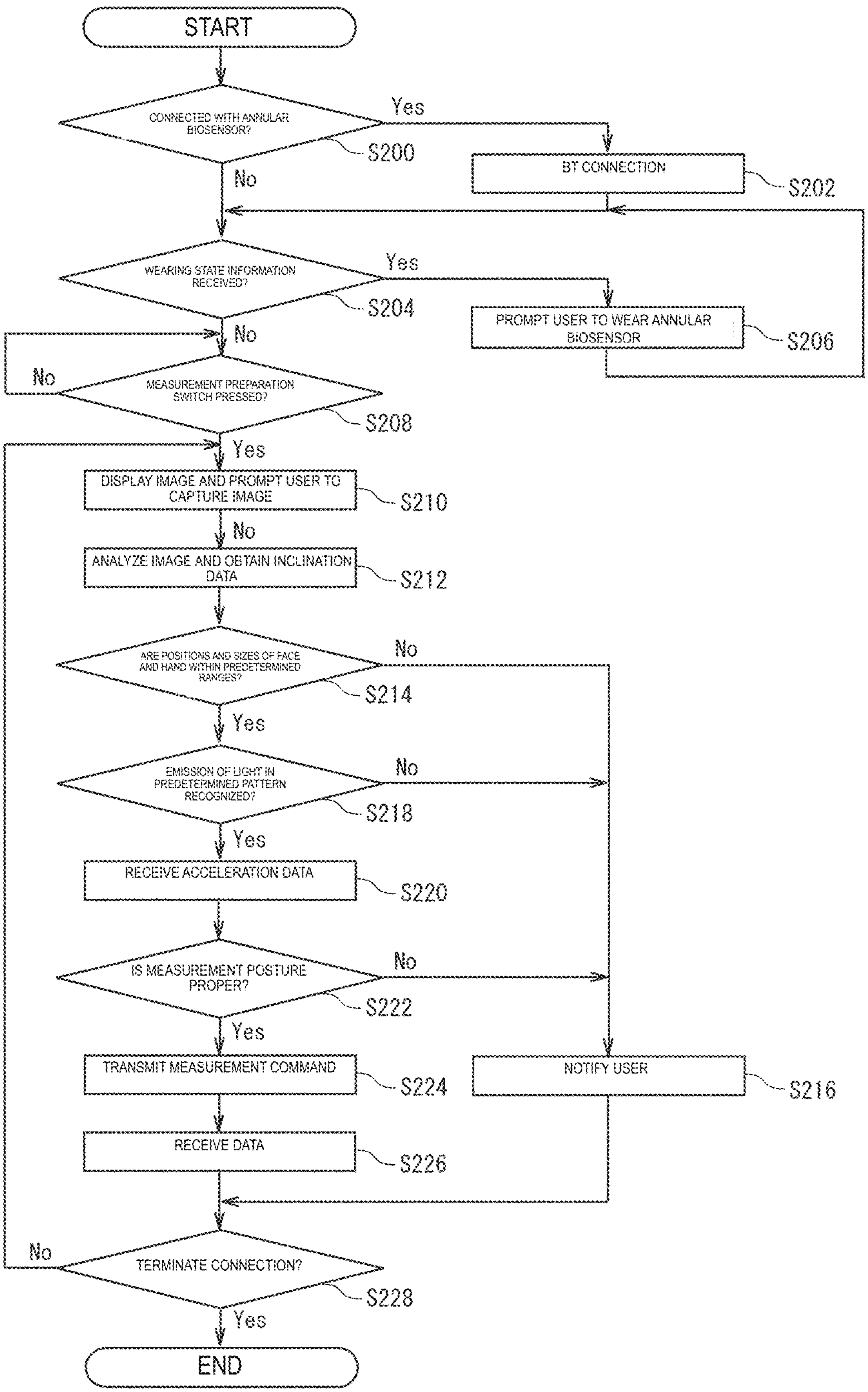
FIG. 10 is a flowchart illustrating a process of measuring, for example, a blood pressure performed by a mobile control unit that includes a biological data measurement system according to an exemplary embodiment.

Next, with reference to FIGS. 9 and 10, operations and methods of the biological data measurement system 1 are described. In particular, FIG. 9 is a flowchart illustrating a process of measuring, for example, a blood pressure performed by the annular biosensor 2 that includes the biological data measurement system 1. Moreover, FIG. 10 is a flowchart illustrating a process of measuring, for example, a blood pressure performed by the mobile control unit 3 that includes the biological data measurement system 1.

In an exemplary aspect, the process illustrated in FIG. 9 is repeatedly performed at a predetermined timing primarily by the annular biosensor 2. The process illustrated in FIG. 10 is repeatedly performed at a predetermined timing primarily by the mobile control unit 3.

First, with reference to FIG. 9, an operation (e.g., blood pressure measurement process) performed by the annular biosensor 2 is described. At step S100, whether the annular biosensor 2 is connected via Bluetooth® to the mobile control unit 3 is determined. When the annular biosensor 2 is not connected to the mobile control unit 3, the process is terminated. On the other hand, when the annular biosensor 2 is connected to the mobile control unit 3, the process proceeds to step S102.

At step S102, a photoplethysmographic signal is obtained. Then, at step S104, whether the annular biosensor 2 is worn on a finger is determined based on the photoplethysmographic signal obtained at step S102. When the annular biosensor 2 is not worn on a finger, the process returns to step S102, and steps S102 and S104 described above are repeated until the annular biosensor 2 is worn on a finger. On the other hand, when the annular biosensor 2 is worn on a finger, the process proceeds to step S106.

At step S106, information (e.g., wearing state information) indicating that the annular biosensor 2 is worn on a finger is transmitted to the mobile control unit 3.

Next, at step S108, whether a measurement preparation command has been received from the mobile control unit 3 is determined. When the measurement preparation command has not been received, the process returns to step S106, and steps S106 and S108 described above are repeated until the measurement preparation command is received. On the other hand, when the measurement preparation command has been received, the process proceeds to step S110.

At step S110, the light-emitting element (light emitter) 221 of the photoplethysmographic sensor 22 starts emitting light in a predetermined pattern.

Next, at step S112, acceleration data (body motion data) is obtained. Then, at step 114, the obtained acceleration data (body motion data) is transmitted to the mobile control unit 3.

Then, at step S116, whether a measurement (start) command has been received from the mobile control unit 3 is determined. When the measurement (start) command has not been received, the process returns to step S110, and steps S110 through S116 described above are repeated until the measurement (start) command is received. On the other hand, when the measurement (start) command has been received, the process proceeds to step S118.

At step S118, photoplethysmographic data (blood pressure data) and acceleration data (body motion data) are obtained. At step S120, the photoplethysmographic data (blood pressure data) and the acceleration data (body motion data) obtained at step S118 are transmitted to the mobile control unit 3. Then, the process is terminated.

Next, an operation (a blood pressure measurement process) performed by the mobile control unit 3 is described with reference to FIG. 10. At step S200, whether the mobile control unit 3 is connected via Bluetooth® to the annular biosensor 2 is determined. When the mobile control unit 3 is not connected to the annular biosensor 2, connection (or pairing) with the annular biosensor 2 is established via Bluetooth® at step S202, and then the process proceeds to step S204. On the other hand, when the mobile control unit 3 is connected to the annular biosensor 2, the process proceeds to step S204.

At step S204, whether information (e.g., wearing state information) indicating that the annular biosensor 2 is worn on a finger has been received from the annular biosensor 2 is determined. When the wearing state information has not been received, information prompting the user to wear the annular biosensor 2 is displayed (or notified) at step S206, and then the process returns to step S204 to determine again whether the wearing state information has been received. On the other hand, when the wearing state information has been received, the process proceeds to step S208.

At step S208, whether a wearing preparation switch has been pressed is determined. When the measurement preparation switch has not been pressed, this step is repeated until the wearing preparation switch is pressed. On the other hand, when the wearing preparation switch has been pressed, the process proceeds to step S210.

At step S210, an image captured by the imager (e.g., camera) 31 is displayed, and information prompting the user to capture an image of the user him/herself is displayed (notified).

Next, at step S212, the image is analyzed to obtain the inclination of the mobile control unit 3 with respect to the vertical direction. Next, at step 214, it is determined whether the position/size of the face in the image, the position/size of the hand wearing the annular biosensor 2, the inclination of the mobile control unit 3 with respect to the vertical direction, and the inclination of the trunk of the user with respect to the vertical direction are within predetermined ranges. When the above values are not within the predetermined ranges, information prompting the user to adjust the above values to fall within the predetermined ranges is displayed (notified) at step S216, and then the process proceeds to step S228. On the other hand, when the values are within the predetermined ranges, the process proceeds to step S218. The methods of recognizing (or determining) the position/size of the face in the image, the position/size of the hand wearing the annular biosensor 2, the inclination of the mobile control unit 3 with respect to the vertical direction, and the inclination of the trunk of the user with respect to the vertical direction are described above. Therefore, detailed descriptions of these methods are omitted here.

At step S218, whether the annular biosensor 2 emitting light in a predetermined light-emission pattern is recognized based on the captured image is determined. When the annular biosensor 2 is not recognized, information prompting the user to place the annular biosensor 2 (the light-emitting element (light emitter) 221 of the photoplethysmographic sensor 22) in the image is displayed (notified) at step S216, and then the process proceeds to step S228. On the other hand, when the annular biosensor 2 is recognized, the process proceeds to step S220.

At step S220, the acceleration data (body motion data) transmitted from the annular biosensor 2 is received (obtained). Then, at step S222, whether the measurement posture is in an appropriate range (whether the annular biosensor 2 is at the height of the chest) and whether the body motion is in an appropriate range are determined. When the measurement posture and the body motion are not in the appropriate ranges, information prompting the user to adjust the measurement posture and the body motion to fall within the appropriate ranges is displayed (or notified) at step S216, and then the process proceeds to step S228. On the other hand, when the measurement posture and the body motion are in the appropriate ranges, the process proceeds to step S224. The method of recognizing (determining) whether the measurement posture is in the appropriate range (whether the annular biosensor 2 is at the height of the chest) is described above, and therefore detailed descriptions of the method are omitted here.

At step S224, a measurement (start) command instructing to start measurement is transmitted to the annular biosensor 2. Then, at step S226, photoplethysmographic data (blood pressure data) and acceleration data (body motion data) transmitted from the annular biosensor 2 are received (obtained). Here, a blood pressure, a blood sugar level, a pulse, oxygen saturation, and breathing are obtained from the photoplethysmographic data. An activity amount and inclination of the annular biosensor 2 are obtained from the acceleration data. Also, when a temperature sensor is provided, a body surface temperature is obtained from temperature data detected by the temperature sensor. Then, the process proceeds to step S228.

At step S228, whether to terminate the connection with the annular biosensor 2 via Bluetooth® is determined. When the connection is to be terminated, the process is terminated after the connection with the annular biosensor 2 via Bluetooth® is terminated. On the other hand, when the connection is not to be terminated, the process returns to step S210, and steps S210 through S228 described above are repeated.

As described in detail above, according to the exemplary aspects of the present embodiment, because the annular biosensor 2, which has an annular shape and includes the sensor 22, is worn on a hand finger or a wrist, the contact pressure (pressing force) on a measurement site is stabilized, and biological data including a blood pressure can be measured accurately. Also, because whether the hand wearing the annular biosensor 2 is at the height of the chest (or heart) is determined based on an image obtained by capturing the face of the user and the hand wearing the annular biosensor 2 and because the annular biosensor 2 is controlled (biological data including a blood pressure is measured) based on the result of determination, biological data including a blood pressure can more accurately be measured. Furthermore, because no cuff is used, the biological data measurement system 1 is highly portable and can non-invasively measure biological data including a blood pressure. Accordingly, the present embodiment provides a biological data measurement system 1 that is highly portable and is configured to more accurately and non-invasively measure biological data that includes a blood pressure, the measurement of which is influenced by the difference between the height of a measurement site and the height of the heart (i.e., influenced by a hydrostatic pressure).

For this purpose, according to the exemplary aspects of the present embodiment, the face of the user in an image is automatically recognized, and the position of the chest (or heart) of the user in the image is estimated based on the display position and the display size of the face. Thus, because the distance between the face and the heart can be estimated based on the size of the face, the accuracy of determining whether the annular biosensor 2 is at the height of the chest is improved.

In general, the exemplary embodiment of the present invention is described above. However, it is noted that the present invention is not limited to the above-described embodiment, and various modifications may be made. For example, although data (e.g., measurement data), such as a measured blood pressure, is sequentially transmitted to the mobile control unit 3 in the present embodiment, the measurement data may be stored in the EEPROM or the RAM of the annular biosensor 2 and may be read later (after measurement).

Although a photoplethysmographic sensor is used as the annular biosensor 2 (the sensor 22) in the above embodiment, the annular biosensor 2 (the sensor 22) is not limited to a photoplethysmographic sensor in alternative aspects.

It is noted that although Bluetooth® is described as a radio communication standard for connecting the annular biosensor 2 to the mobile control unit 3 in the above exemplary embodiment, any other radio communication standard such as Bluetooth Low Energy (BLE) may be used instead of Bluetooth®.

REFERENCE SIGNS LIST

1 biological data measurement system
2 annular biosensor
21 body
211 light state variable component
22 sensor (photoplethysmographic sensor)
221 light-emitting element (sensor-side light emitter)
222 light-receiving element
23 sensor-side communicator
24 determiner
25 acceleration sensor
3 mobile control unit
31 imager
32 display (unit-side light emitter)
33 unit-side communicator
34 controller
35 inclination sensor (acceleration sensor)

The invention claimed is:

1. A biological data measurement system comprising:
an annular biosensor including:
a body having an annular shape and that is configured to be worn on a finger or a wrist of a user,
a sensor disposed in the body and configured to measure biological data including a blood pressure of the user, and
a light emitter disposed in the body of the annular biosensor and configured to emit light in a predetermined pattern, wherein the light emitter commences emitting light in the predetermined pattern when a measurement preparation command is received, and wherein the predetermined pattern is a light intensity change pattern that changes an intensity of emitted light with time; and
a mobile control unit configured to communicate with the biosensor and including:
an imager configured to capture images,
a display configured to prompt the user holding the mobile control unit in a first hand to cause the imager to capture an image of a face of the user and a second hand that is wearing the annular biosensor and to display the image captured by the imager, and
a controller configured to:
detect, in the image, the predetermined pattern of light emitted by the light emitter and configured to recognize a position of the annular biosensor in the image based on the detected pattern, and
determine, based on the image, whether the second hand wearing the annular biosensor is at a height of a chest of the user, and also to control the biological data measurement system to obtain the biological data based on the determining of whether the second hand wearing the annular biosensor is at the height of the chest of the user.

2. The biological data measurement system according to claim 1, wherein:
a surface of the body of the annular biosensor comprises an identification marking that includes at least one of a letter, a symbol, a one-dimensional code, or a two-dimensional code, the identification marking recognizable in the image captured by the imager of the mobile control unit, and
the controller is configured to recognize a position of the annular biosensor in the image by recognizing the identification marking.

3. The biological data measurement system according to claim 1, wherein:
the body of the annular biosensor has a shape that is recognizable in the image, and
the controller is configured to recognize a position of the annular biosensor in the image by recognizing the shape of the body in the image.

4. The biological data measurement system according to claim 1, wherein:
a surface of the body of the annular biosensor includes a light state variable component configured to reflect, scatter, or absorb light, and
the controller is configured to recognize a position of the annular biosensor in the image by recognizing the light state variable component in the image.

5. The biological data measurement system according to claim 3, wherein:
the mobile control unit includes a unit-side light emitter configured to emit light in a predetermined pattern, and
the controller is configured to recognize the position of the annular biosensor in the image by recognizing the annular biosensor reflecting or scattering the light emitted in the predetermined pattern in the image.

6. The biological data measurement system according to claim 1, wherein:
the light emitter is disposed on a sensor-side.

7. The biological data measurement system according to claim 6, wherein:
the sensor of the annular biosensor is a photoplethysmographic sensor including a light-emitting element and a light-receiving element,
the sensor-side light emitter is the light-emitting element of the photoplethysmographic sensor, and
a directivity angle of the light-emitting element of the photoplethysmographic sensor is greater than a directivity angle of the light-receiving element of the photoplethysmographic sensor.

8. The biological data measurement system according to claim 1, wherein the controller is configured to recognize the face of the user in the image and to estimate a position of the chest of the user in the image based on a display position and a display size of the face.

9. The biological data measurement system according to claim 8, wherein the controller is configured to obtain prestored physical information of the user and to estimate the position of the chest of the user based at least partially on the prestored physical information.

10. The biological data measurement system according to claim 8, wherein the controller is configured to recognize the face of the user and the second hand wearing the annular biosensor in the image, to estimate a relative position between the mobile control unit and a trunk of the user based on a ratio between the display size of the face of the user and a display size of the second hand, and to determine whether the relative position is within a predetermined range.

11. The biological data measurement system according to claim 1, wherein the display of the mobile control unit is configured to graphically display a recommended range of a display position of the face and a display size of the face.

12. The biological data measurement system according to claim 11, wherein:
the controller is configured to recognize the face of the user in the image, and
the display is configured to inform the user whether the display position of the face and the display size of the face are within the recommended range.

13. The biological data measurement system according to claim 1, wherein the biological data further includes at least one of a blood sugar level, a pulse, breathing, a pulse wave, oxygen saturation, a body surface temperature, and an activity amount.

14. The biological data measurement system according to claim 10, wherein:

the mobile control unit includes an inclination sensor configured to detect an inclination of the mobile control unit with respect to a vertical direction, and the controller is configured to determine whether an inclination of the trunk of the user with respect to the vertical direction and a lateral direction is within a predetermined range based on the inclination of the mobile control unit with respect to the vertical direction detected by the inclination sensor.

15. The biological data measurement system according to claim 14, wherein the controller is configured to recognize the face of the user and the second hand wearing the annular biosensor in the image, to estimate the relative position between the mobile control unit and the trunk of the user based on the display size of the face of the user and the display size of the second hand, and to determine whether the inclination of the trunk of the user with respect to the vertical direction and a forward-backward direction is within a predetermined range based on the inclination of the mobile control unit detected by the inclination sensor and the relative position between the mobile control unit and the trunk of the user.

16. The biological data measurement system according to claim 14, wherein the controller is configured to recognize the face of the user and the second hand wearing the annular biosensor in the image, to estimate the relative position between the mobile control unit and the trunk of the user based on the display size of the face of the user and the display size of the second hand, to determine whether the inclination of the trunk of the user with respect to the vertical direction is within a predetermined range based on a result of the estimation and the inclination of the mobile control unit detected by the inclination sensor, and to control the annular biosensor based on a result of the determination.

17. The biological data measurement system according to claim 14, wherein the display is configured to display information indicating whether the relative position between the mobile control unit and the trunk of the user and the inclination of the trunk of the user are within predetermined ranges.

18. The biological data measurement system according to claim 14, wherein:

the annular biosensor includes:

a determiner configured to determine whether the annular biosensor is worn on the finger or the wrist of the user, and a sensor-side communicator configured to transmit and receive data to and from the mobile control unit, the sensor-side communicator is further configured to transmit a result of determining whether the annular biosensor is worn on the finger or the wrist, and the controller is configured to prevent a determination of the inclination of the trunk of the user when the annular biosensor is not worn on the finger or the wrist.

19. The biological data measurement system according to claim 14, wherein the controller is further configured to calculate a reliability level of the obtained biological data based on a result of determining the inclination of the trunk of the user with respect to the vertical direction.

20. The biological data measurement system according to claim 14, wherein the controller is configured to correct the biological data based on a result of determining the inclination of the trunk of the user with respect to the vertical direction.

* * * * *